United States Patent [19]

Van Horn et al.

[11] 4,178,457

[45] Dec. 11, 1979

[54] (DL)-16-PHENOXY- AND 16-SUBSTITUTED PHENOXY-9-KETO PROSTATRIENOIC ACID DERIVATIVES AND PROCESSES FOR THE PRODUCTION THEREOF

[75] Inventors: Albert R. Van Horn, Los Altos; Gabriel Garay, Sunnyvale; John A. Edwards, Los Altos, all of Calif.

[73] Assignee: Syntex (U.S.A.) Inc., Palo Alto, Calif.

[21] Appl. No.: 922,957

[22] Filed: Jul. 10, 1978

[51] Int. Cl.$^2$ .......................................... C07C 177/00
[52] U.S. Cl. ...................................... 560/53; 562/463
[58] Field of Search ......................... 560/53; 562/463

[56] References Cited

U.S. PATENT DOCUMENTS 3,985,791  10/1976  Fried .................................. 260/473

*Primary Examiner*—Paul J. Killos
*Attorney, Agent, or Firm*—Gerard A. Blaufarb; Alan M. Krubiner

[57] ABSTRACT

Novel 16-phenoxy and 16-(o, m or p)-substituted phenoxy derivatives of (dl)-9-keto-11α,15α-dihydroxy-17,18,19,20-tetranorprosta-4,5,13-trans-trienoic acid, the pharmaceutically acceptable, non-toxic lower alkyl esters and salts thereof and processes for the production of such compounds. These compounds possess prostaglandin-like activities and thus are useful in the treatment of mammals where prostaglandins are indicated. They are particularly useful as inhibitors of gastric acid secretion; and as agents for the control of asthmatic attack, because of their bronchodilating activity.

10 Claims, No Drawings

(DL)-16-PHENOXY- AND 16-SUBSTITUTED PHENOXY-9-KETO PROSTATRIENOIC ACID DERIVATIVES AND PROCESSES FOR THE PRODUCTION THEREOF

DESCRIPTION OF THE INVENTION

The present invention relates to certain novel prostaglandin analogs and to the process for the production thereof.

More particularly, the present invention relates to 16-phenoxy- and 16-(o, m or p)-substituted phenoxy derivatives of (dl)-9-keto-11α,15α-dihydroxy-17,18,19,20-tetranorprosta-4,5,13-trans-trienoic acid, as well as the pharmaceutically acceptable, non-toxic lower alkyl esters and salts thereof and to processes for producing such compounds.

Prostaglandins have classically been described as chemically related 20 carbon chain hydroxy fatty acids having the basic skeleton of prostanoic acid:

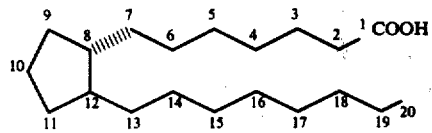

The prostaglandins having a hydroxyl group at the C-11 position and a keto group at the C-9 position are known as the PGE series, those having a hydroxyl group in place of the keto group are known as the PGF series and are further designated by an α or β suffix to indicate the configuration of the hydroxyl group at said position. The natural compounds are the α-hydroxy substituted compounds. They may contain different degrees of unsaturation in the molecule, particularly at C-5, C-13 and C-17, the unsaturation is also indicated by a suffix. Thus, for example, the $PGF_1$ and $PGE_1$ series refer to prostanoic acids having a trans olefin bond at the C-13 position, while the $PGF_2$ and $PGE_2$ series refer to prostadienoic acids having a cis-olefin bond at the C-5 position and a trans olefin bond at the C-13 position. For a review on prostaglandins and the definition of primary prostaglandins, see for example, S. Bergstrom, Recent Progress in Hormone Research 22, pp. 153–175 (1966) and Science 157, page 382 (1967) by the same author.

The preparation of derivatives of prostanoic acid has become of great importance since the demonstration of the highly interesting range of biological and pharmacological activities of natural prostaglandins.

The great majority of these studies have focused on modification of the two side chains, or modifications of the substituents attached to the cyclopentane moiety [see, for example, U. Axen et al., Synthesis Vol. 1, John Wiley and Sons Inc., New York, N.Y. 1973 and P. H. Bently, Chem. Soc. Reviews, 2, 29 (1973)]. The synthesis of prostaglandin analogs having diethylenic (allenic) unsaturation in the carboxylic acid chain has been described, among others, in U.S. Pat. No. 3,879,438, issued Apr. 22, 1975, of Crabbe and Fried. The synthesis of several prostaglandin analogs in which the alkyl chain attached to C-15 in the natural compounds is replaced by an aryloxymethylene group has been reported in, for example, U.S. Pat. Nos. 3,864,387, 3,954,881 (9-keto-16-phenoxy-5,13-prostadienoic compounds), 3,985,791 (9α-hydroxy-16-phenoxy-4,5,13-prostatrienoic compounds) and Belgium Patent No. 806,995.

In accordance with the present invention we have prepared certain novel 16-phenoxy- and 16-substituted phenoxy-9-keto-prostaglandin analogs represented by the following formula:

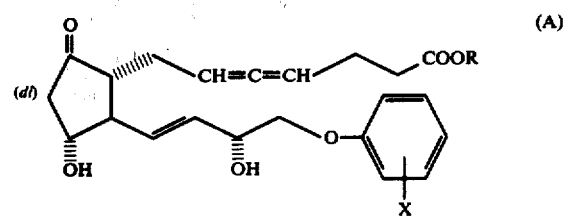

wherein

R is hydrogen, a lower alkyl group of 1 to 4 carbon atoms, or the pharmaceutically acceptable, non-toxic salts of compounds in which R is hydrogen; and X is hydrogen, o-, m- or p-halo (fluoro, chloro or bromo), o-, m- or p-methyl or o-, m- or p-methoxy.

The lines shown in the above formula and in the formulas below as "≡" indicate that the substituents are in α configuration, i.e., below the plane of the cyclopentane ring.

The double bond at C-13 in the compounds of the present invention has the same configuration as in natural prostaglandins of the PGE and PGF series, that is the trans configuration.

These novel compounds possess asymmetric centers and thus can be produced as racemic "(dl)" mixtures or as individual 8R-antimers. The racemic mixtures can be resolved if desired at appropriate stages by methods known to those skilled in the art, to obtain the respective individual antimers.

The term "lower alkyl" as used herein, unless otherwise specified, refers to straight or branched alkyl groups containing up to 4 carbon atoms, e.g., methyl, ethyl, n-propyl, isopropyl, n-butyl, and the like.

The term "pharmaceutically acceptable salts" refers to salts prepared from pharmaceutically acceptable non-toxic bases, including inorganic bases and organic bases. Salts derived from inorganic bases include sodium potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, lysine, arginine, histidine, caffeine, procaine, hydrabamine, choline, betaine, ethylenediamine, glucosamine, N-methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, choline and caffeine.

The novel 9-keto compound of the present invention can be obtained by a process illustrated by the following sequence of reactions:

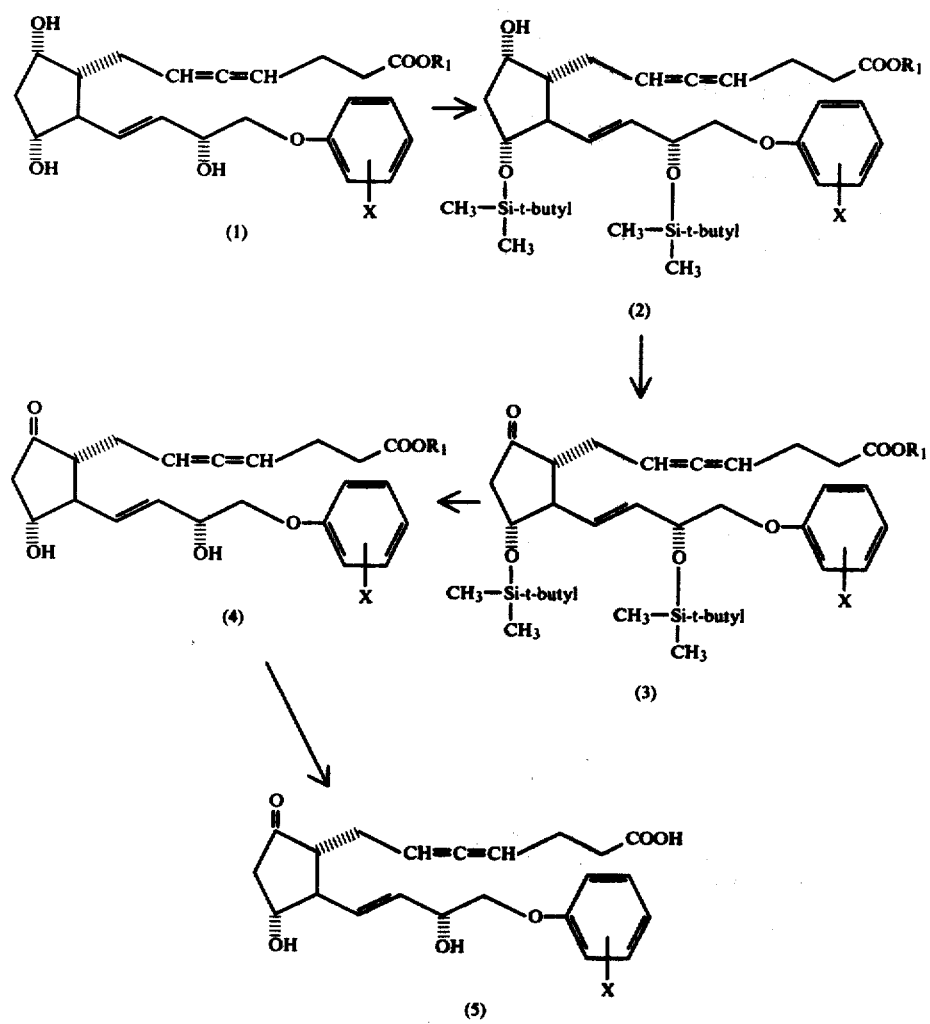

wherein

X has the above-indicated meaning; and $R_1$ is a lower alkyl group of 1 to 4 carbon atoms.

The starting compounds of Formula (1) can be prepared according to the procedures set forth in U.S. Pat. No. 3,985,791, which procedures are hereby incorporated by reference and made a part hereof.

The compounds of Formula (1), preferably where $R_1$ is methyl, are treated with t-butyldimethylsilyl halide, preferably t-butyldimethylsilyl chloride, in the presence of imidazole, N-methyl imidazole, and the like, preferably imidazole, in the presence of an organic solvent e.g., dimethylformamide, dimethylacetamide, pyridine, and the like, preferably dimethylformamide, or mixtures thereof, at a temperature of from about −40° C. to about −10° C., preferably from about −30° C. to about −20° C., for from about 5 to about 24 hours, preferably from about 15 to about 20 hours, to obtain the 9-keto-11α,15α-bis-t-butyldimethylsilyloxy compounds of Formula (2). Any mono- and/or trisilyloxy compounds which forms can be hydrolyzed, as described more fully below, to obtain the compounds of Formula (1) for recycling as starting materials.

The compounds of Formula (2) are then treated with an oxidizing agent, e.g. chromium trioxide, pyridine dichromate, and the like, preferably chromium trioxide, in the presence of pyridine, hexamethylphosphoric triamide, 3,5-dimethylpyrazole, and the like, preferably pyridine, or pyridinium chlorochromate with sodium acetate, and an organic solvent, e.g., dichloromethane, dichloroethane, and the like, preferably dichloromethane, or mixtures thereof, at a temperature of from about −10° C. to about 30° C., preferably from about 15° C. to about 25° C., for from about 30 minutes to about 2 hours, preferably from about 15 minutes to about 45 minutes, to obtain the 9-keto-11α,15α-bis-t-butyldimethylsilyloxy compounds of Formula (3). Advantageously, this reaction is carried out under anhydrous conditions under an inert atmosphere, e.g., nitrogen gas.

The compounds of formula (4) are obtained by hydrolysis of the compounds of Formula (3), preferably acid hydrolysis with an organic or mineral acid, for example, acetic acid, monochloroacetic acid, propionic acid, and the like, or mixtures thereof, preferably acetic acid, at a temperature of from about 0° C. to about 35° C., preferably from about 15° C. to about 25° C., for from about 10 to about 24 hours, preferably from about 15 to about 20 hours.

The further hydrolysis of the compounds of Formula (4) to obtain the free acid compounds of Formula (5), the 9-keto-11α,15α-dihydroxy free acids, is carried out biologically, preferably enzymatically, using a pancreatic lipase preparation to cleave the ester (preferably the methyl ester) group, thus yielding the free acid.

Alternatively, the compounds of Formula (5) can be converted into their corresponding alkyl esters by methods known in the art, i.e., by treatment of the free acid with an excess of a diazoalkane, such as diazomethane, diazoethane or diazopropane in ether or methylene chloride solution, in a conventional manner.

The salt derivatives of the 9-keto-prostatrienoic free acids of the present invention, as depicted by Formula (5), can be prepared by treating the corresponding free acids with about one molar equivalent of a pharmaceutically acceptable base, including inorganic and organic bases per molar equivalent of free acid. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylamine, lysine, arginine, histidine, caffeine, procaine, hydrabamine, chloine, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, piperidine, tromethamine, chloine and caffeine.

The reaction is conducted in water, alone or in combination with an inert, water-miscible organic solvent, at a temperature of from about 0° C. to about 100° C., preferably at room temperature. Typical inert, water miscible organic solvents include methanol, ethanol, isopropanol, butanol, acetone, dioxane or tetrahydrofuran. The molar ratio of the free acid to base used are chosen to provide the ratio desired for any particular salt. For preparing, for example, the calcium salts or magnesium salts, the free acid starting material can be treated with at least 0.5 molar equivalent of pharmaceutically acceptable base to yield a neutral salt. When the aluminum salts are prepared, at least one third molar equivalent of the pharmaceutically acceptable base are employed if a neutral salt product is desired.

In the preferred procedure, the calcium salts and magnesium salts of the prostatrienoic acid compounds hereof can be prepared by treating the corresponding sodium or potassium salts with at least 0.5 molar equivalent of calcium chloride or magnesium chloride, respectively, in an aqueous solution, alone or in combination with an inert water miscible organic solvent, at a temperature of from about 20° C. to about 100° C. Preferably, the aluminum salts of the prostatrienoic acids of the present invention can be prepared by treating the corresponding free acids with at least one third molar equivalent of an aluminum alkoxide, such as aluminum triethoxide, aluminum tripropoxide and the like, in a hydrocarbon solvent, such as benzene, xylene, cyclohexane and the like, at a temperature of from 20° C. to about 80° C. Similar procedures can be used to prepare salts of inorganic bases which are not sufficiently soluble for easy reaction.

The salt products are isolated by conventional methods.

The compounds of the present invention exhibit prostaglandin-like biological activities and thus are used in the treatment of mammals where the use of prostaglandins is indicated. The compounds of the present invention are useful for the control of asthmatic attack because they are bronchodilators and they also exhibit anti-allergic properties by inhibition of mediator release. In addition, they are also useful in treating mammals for bronchial spasm or wherever bronchodilators are indicated. The compounds also exhibit vasodilator properties and are useful in controlling or palliating hypertension in mammals and they further exhibit central nervous system depressant activity in mammals, and are useful as sedatives.

More particularly, and surprisingly, these 9-keto-16-phenoxy-4,5,13-prostatrienoic compounds, of Formula (I), have unexpectedly been found to be more potent inhibitors of gastric secretion and ulcer induction than the corresponding 9-keto-16-phenoxy 5,13-prostadienoic compounds. Thus, the compounds of Formula (I) are extremely useful in the treatment and prevention of gastric and duodenal ulcers.

The present compounds can be administered in a wide variety of dosage forms, either alone or in combination with other pharmaceutically compatible medicaments, in the form of pharmaceutical compositions suited for oral or parenteral administration or inhalation in the case of bronchodilators. They are typically administered as pharmaceutical compositions consisting essentially of the free acid, salt or ester of the invention and a pharmaceutical carrier. The pharmaceutical carrier can be either a solid material, liquid or aerosol, in which the compound (free acid, salt or ester) is dissolved, dispersed or suspended, and can optionally contain small amounts of preservatives and/or pH buffering agents. Suitable preservatives which can be used include, for example, benzyl alcohol and the like. Suitable buffering agents include, for example, sodium acetate and pharmaceutical phosphate salts and the like.

The liquid compositions can, for example, be in the form of solutions, emulsions, suspensions, syrups, or elixirs. The solid compositions can take the form of tablets, powders, capsules, pills or the like, preferably in unit dosage forms for simple administration or precise dosages. Suitable solid carriers include, for example, pharmaceutical grades of starch, lactose, sodium saccharine, talcum, sodium bisulfite and the like.

For inhalation administration, the free acids, salts and esters can, for example, be administered as an aerosol comprising the compounds or salts in an inert propellant together with a cosolvent, e.g., methanol, together with optional preservatives and buffering agents. Additional general information concerning the inhalation administration of aerosols can be had by reference to U.S. Pat. Nos. 2,868,691 and 3,095,355.

The compounds of this invention are typically administered in dosages of about from about 1 $\mu$g. to about 100 $\mu$g. per Kg. of body weight. The precise effective dosage will, of course, vary depending upon the mode of administration, condition being treated and host. Thus, for example, to achieve bronchodilation about 1 $\mu$g. to about 10 $\mu$g. per Kg. of body weight is administered by aerosol, and to achieve inhibition of gastric secretions about 1 $\mu$g. to about 50 $\mu$g. per Kg. of body weight is administered orally.

DESCRIPTION OF SPECIFIC EMBODIMENTS

The following specific description, recited in the Preparation and Examples below, is given to enable those skilled in this art to more clearly understand and practice the present invention. It should not be considered as a limitation upon the scope of the invention but merely as being illustrative and representative thereof.

It is to be understood that isolation of the compounds described herein can be effected by any suitable separation or purification procedure, such as, for example, extraction, filtration, evaporation, distillation, crystallization, thin-layer chromatography, high pressure liquid chromatography, or column chromatography, or a combination of these procedures. Illustrations of suitable separation and isolation procedures can be had by reference to the Preparation and Examples described herein below. However, other equivalent separation or isolation procedures, could, of course, also be used.

PREPARATION 1

This preparation illustrates methods of preparing a pancreatic lipase preparation which can be used to convert the compounds of Formula (4) to the compounds of Formula (5). In this preparation, 10 g. of crude pancreatic lipase [note: *Biochem. Biophysics Acta.*, v. 23, p. 264 (1957)] is suspended in 65 ml. of water at 0° C. The suspension is stirred for one hour at 0° C. and then centrifuged for 20 minutes at 10,000×g. The supernatant liquid is separated and maintained at 0° C. for later use. The precipitate is again suspended in 65 ml. of water at 0° C. and centrifuged as before. The supernatant liquid is separated and combined with the previously obtained supernatant liquid and then added to 130 ml. of saturated aqueous ammonium sulfate solution at 0° C., with stirring, and then allowed to stand for five minutes. The resulting mixture is then centrifuged at 10,000×g. for 20 minutes. The supernatant liquid is decanted and the precipitate is collected, then dissolved in sufficient water to yield 125 ml of solution. 15 Ml. of saturated aqueous ammonium sulfate solution is then added to the water solution yielding a suspension which is then centrifuged at 10,000×g. for 20 minutes. The supernatant liquid is collected and treated with 100 ml. of saturated ammonium sulfate affording a second suspension, which is divided into two equal portions. Each portion is again centrifuged for 20 minutes at 10,000×g., and in each instance the supernatant liquid is discarded (decantation) and the precipitate collected. Each precipitate is stored at 4° C. prior to use.

The pancreatic lipase ester cleaving preparation is then prepared immediately prior to use by dissolving one of the above precipitates in 25 ml. of an aqueous 0.1 M sodium chloride solution and 0.05 M calcium chloride solution and then adjusting the pH to 7.0 by the careful addition (i.e. titration) of a 0.1 M aqueous sodium hydroxide solution.

EXAMPLE 1

To a solution of 0.50 g. of (dl)-9α,11α,15α-trihydroxy-16-phenoxy-17,18,18,20-tetranorprosta-4,15,13-trans-trienoic acid methyl ester (1) having the following physical constants:

U.V. λ max./MeOH 220, 265, 271, 278 nm (log ε 3.99, 3.11, 3.23, 3.16) (ε 1972, 1284, 1710, 1437);
N.M.R. δ TMS/CDCl$_3$ 3.62 (s, 3H, OCH$_3$),
3.89 (m, 1h, H-11),
3.92 (d, 2h, H-16, J=6),
4.20 (m, 1H, H-9),
4.46 (m, 1H, H-15),
5.11 (m, 2H, H-4,6),
5.62 (m, 2H, H-13, 14),
6.8–7.0 (m, 3H, aromatic-H),
7.15–7.25 (m, 2H, aromatic-H);
C-13 N.M.R. δ (ppm) 23.83, 24.06 (C-3), 27.15 (C-7), 33.22 (C-2), 42.59, 42.72 (C-10), 49.51, 49.77 (C-8), 51.72 (OCH$_3$), 55.79 (C-12), 71.07 (C-15), 71.85 (C-16), 72.40 72.53 (C-9), 77.70 (C-11), 89.92, 90.15 (C-6), 90.96 (C-4), 114.82 (C-18), 121.33 (C-20), 129.68 (C-19), 130.36 (C-14), 135.14 (C-13), 158.71 (C-17), 173.80, 173.89 (C-1), 204.32 (C-5); and M.S. m/e 402 (M+), and 0.45 g. of imidazole in 19 ml. of dry dimethylformamide stirring at −25° C., there is added 0.50 g. t-tubyldimethylsilyl chloride. The reaction solution is stirred at −30° C. to −20° C. for 16 hours, 250 ml. of diethyl ether is added and the diethyl ether solution is washed with two 50 ml. portions of water. The diethyl ether solution is dried over anhydrous sodium sulfate and evaporated under reduced pressure to yield (dl)-9α-hydroxy-11α,1-5α-bis-t-butyldimethylsilyloxy-16-phenoxy-17,18,19,20-tetranorprosta-4,5,13-trans-trienoic acid methyl ester (2) and a small amount of the tri- and mono-t-butyldimethylsilyloxy analogs corresponding thereto. The crude reaction mixture is chromatographed on a column containing 100 g. of silica gel and eluted with ethyl acetate-hexane (15:85) to yield (dl)-9α-hydroxy-11α,15α-bis-t-butyldimethylsilyloxy-16-phenoxy-17,18,19,20-tetranorprosta-4,5,13-trans-trienoic acid methyl ester (2) having the following physical constants:

N.M.R. δ $_{TMS}$CDCl$_3$ 0.85 (s, 9H, OSiC(CH$_3$)$_2$t-Bu),
0.89 (s, 9H, OSiC(CH$_3$)$_2$t-Bu), 3.62 (s, 3H, OCH$_3$),
3.81 (d, 2H, H-16, J=16),
3.95 (m, 1H, H-11),
4.17 (m, 1H, H-9),
4.47 (m, 1H, H-15),
5.14 (m, 2H, H-4,6),
6.78–7.0 (m, 3H, aromatic-H),
7.15–7.35 (m, 2H, aromatic-H); and
M.S. m/e 645 (M+ −C$_4$H$_9$).

The more polar mononsilylated and less polar trisilylated chromatographic fractions can be transformed back into the starting triol materials of Formula (1) for subsequent conversion to the compounds of Formula (2) using, for example, the following hydrolysis procedure: A solution of 0.2–1.0 g. of the mono- and-trisilyl derivatives otherwise corresponding to compound(s) described above, in 250 mol. of acetic acid-water (65/35; vol./vol.) is stirred at ambient temperature for 15–20 hours. The acetic acid-water is removed under reduced pressure followed by azeotropic vacuum distillation using 100 ml. of toluene. The thus-obtained regenerated triol (1) can then be directly transfored into its 11α,15α-bis-t-butyl-dimethylsilyloxy derivative (2) as described above.

In like manner, substituting a stoichiometric equivalent amount of the methyl esters of
(dl)-9α,11α,15α-trihydroxy-16-o-fluorophenoxy-17,18,19, 20-tetranorprosta-4,5,13-trans-trienoic acid,
(dl)-9α,11α,15α-trihydroxy-16-m-fluorophenoxy-17,18,19, 20-tetranorprosta-4,5,13-trans-trienoic acid,
(dl)-9α,11α,15α-trihydroxy-16-p-fluorophenoxy-17,18,19, 20-tetranorprosta-4,5,13-trans-trienoic acid,
(dl)-9α,11α,15α-trihydroxy-16o-chlorophenoxy-17,18,19, 20-tetranorprosta-4,5,13-trans-trienoic acid,
(dl)-9α11α,15α-trihydroxy-16-m-chlorophenoxy-17,18,19, 20-tetranorprosta-4,5,13-trans-trienoic acid, (dl)-9α,11α,15α-trihydroxy-16-m-chlorophenoxy-
17,18,19, 20-tetranprosta-4,5,13-trans-trienoic acid,
(dl)-9α,11α,15α-trihydroxy-16-o-bromophenoxy-
17,18,19, 20-tetranorprosta-4,5,13-trans-trienoic acid,
(dl)-9α,11α,15α-trihydroxy-16-m-bromophenoxy-
17,18,19, 20-tetranorprosta-4,5,13-trans-trienoic acid,
(dl)-9α,11α,15α-trihydroxy-16-p-bromophenoxy-
17,18,19, 20-tetranorprosta-4,5,13-trans-trienoic acid,
(dl)-9α,11α,15α-trihydroxy-16-o-methylphenoxy-
17,18,19, 20-tetranorprosta-4,5,13-trans-trienoic acid,
(dl0-9α,11α,15α-trihydroxy-16-m-methylphenoxy-
17,18,19, 20-tetranorprosta-4,5,13-trans-trienoic acid,
(dl)-9α,11α,15α-trihydroxy-16-p-methylphenoxy-
17,18,19, 20-tetranorprosta-4,5,13-trans-trienoic acid,
(dl)-9α,11α,15α-trihydroxy-16-o-methoxyphenoxy-
17,18, 19,20-tetranorprosta-4,5,13-trans-trienoic acid,
(dl)-9α,11α,15α-trihydroxy-16-m-methoxyphenoxy-
17,18, 19,20-tetranorprosta-4,5,13-trans-trienoic acid,
and
(dl)-9α,11α,15α-trihydroxy-16-p-methoxyphenoxy-
17,18, 19,20-tetranorprosta-4,5,13-trans-trienoic acid,
for the methyl ester of (dl)-9α,11α,15α-trihydroxy-16-phenoxy-17,18,19,20-tetranorprosta-4,5,13-trans-trienoic acid, there are obtained the methyl esters of
(dl)-9α-hydroxy-11α,15α-bis-t-butyldimethylsilyloxy-
16-o-fluorophenoxy-17,18,19,20-tetranorprosta-
4,5,13-trans-trienoic acid,
(dl)-9α-hydroxy-11α,15α-bis-t-butyldimethylsilyloxy-
16-m-fluorophenoxy-17,18,19,20-tetranorprosta-
4,5,13-trans-trienoic acid,
(dl)-9α-hydroxy-11α,15α-bis-t-butyldimethylsilyloxy-
16-p-fluorophenoxy-17,18,19,20-tetranoprosta-4,5,13-trans-trienoic acid,
(dl)-9α-hydroxy-11α,15α-bis-t-butyldimethylsilyloxy-
16-o-chlorophenoxy-17,18,19,20-tetranorprosta-
4,5,13-trans-trienoic acid,
(dl)-9α-hydroxy-11α,15α-bis-t-butyldimethylsilyloxy-
16-m-chlorophenoxy-17,18,19,20-tetranorprosta-
4,5,13-trans-trienoic acid,
(dl)-9α-hydroxy-11α,15α-bis-t-butyldimethylsilyloxy-
16-p-chlorophenoxy-17,18,19,20-tetranorprosta-
4,5,13-trans-trienoic acid,
(dl)-9α-hydroxy-11α,15α-bis-t-butyldimethylsilyloxy-
16-o-bromophenoxy-17,18,19,20-tetranorprosta-
4,5,13-trans-trienoic acid,
(dl)-9α-hydroxy-11α,15α-bit-t-butyldimethylsilyloxy-
16-m-bromophenoxy-17,18,19,20-tetranorprosta-
4,5,13-trans-trienoic acid,
(dl)-9α-hydroxy-11α,15α-bis-t-butyldimethylsilyloxy-
16-p-bromophenoxy-17,18,19,20-tetranorprosta-
4,5,13-trans-trienoic acid,
(dl)-9α-hydroxy-11α,15α-bis-t-butyldimethylsilyloxy-
16-o-methylphenoxy-17,18,19,20-tetranorprosta-
4,5,13-trans-trienoic acid,
(dl)-9α-hydroxy-11α,15α-bis-t-butyldimethylsilyloxy-
16-m-methylphenoxy-17,18,19,20-tetranorprosta-
4,5,13-trans-trienoic acid,
(dl)-9α-hydroxy-11α,15α-bis-t-butyldimethylsilyloxy-
16-p-methylphenoxy-17,18,19,20-tetranorprosta-
4,5,13-trans-trienoic acid,
(dl)-9α-hydroxy-11α,15α-bis-t-butyldimethylsilyloxy-
16-o-methoxyphenoxy-17,18,19,20-tetranorprosta-
4,5,13-trans-trienoic acid,
(dl)-9α-hydroxy-11α,15α-bis-t-butyldimethylsilyloxy-
16-m-methoxyphenoxy-17,18,19,20-tetranorprosta-
4,5,13-trans-trienoic acid, (dl)-9α-hydroxy-11α,15α-bis-t-butyldimethylsilyloxy-
16-p-methoxyphenoxy-17,18,19,20-tetranorprosta-;b
4,5,13-trans-trienoic acid, respectively.

In like manner other esters otherwise corresponding to the above-identified compounds can be converted into the corresponding ester 11α,15α-bis-t-butyldimethylsilyloxy compounds.

EXAMPLE 2

0.77 G. of anhydrous chromium trioxide is added to a stirred solution of 1.5 ml. of dry pyridine in 20 ml. of dry dichloromethane and stirred under a dry nitrogen atmosphere at 20° C. for 15 minutes after which a solution of 305 mg. of (dl)-9α-hydroxy-11α,15α-bis-t-butyldimethylsilyloxy-16-phenoxy-17,18,19,20-tetranorprosta-4,5,13-trans-trienoic acid methyl ester (2) in 10 ml. of dry dichloromethane is added and the reaction mixture is stirred for 30 minutes at 20° C. The solution is decanted from the residue and the residue is washed with two 200 ml. portions of diethyl ether. The organic solutions are combined, washed successively with three 50 ml. portions of water and dried over anhydrous sodium sulfate. Evaporation under reduced pressure gives an oily residue which is chromatographed on a silica gel column, eluting with ethyl acetate-hexane (15:85), to yield (dl)-9-keto-11α,15α-bis-t-butyl-dimethylsilyloxy-16-phenoxy-17,18,19,20-tetranorprosta-4,5,13-trans-trienoic acid methyl ester (3) having the following physical constants:

U.V. $\lambda_{max.}^{MeOH}$ 220, 245, 263, 270, 277 nm (log ε 4.04, 3.34, 3.30, 3.33, 3.21) (ε 11089, 2191, 1997, 2116, 1639);

N.M.R. $\delta_{TMS}^{CDCl_3}$ 0.86 (s, 9H, OSi(CH$_3$)$_2$t-Bu),
0.89 (s, 9H, OSi(CH$_3$)$_2$t-Bu),
3.62 (s, 3H, OCH$_3$),
3.83 (d, 2H, H-16, J=6),
4.08 (q, 1H, H-11, J=8)
4.54 (m, 1H, H-15),
5.09 (m, 2H, H-4,6),
5.71 (m, 2H, H-13, 14),
6.78–7.0 (m, 3H, aromatic-H),
7.15–7.35 (m 2H, aromatic-H); and
M.S. m/e 628 (M+).

In like manner, substituting a stoichiometric equivalent amount of the methyl esters of
(dl)-9α-hydroxy-11α,15α-bis-t-butyldimethylsilyloxy-
16-o-fluorophenoxy-17,18,19,20-tetranorprosta-
4,5,13-trans-trienoic acid,
(dl)-9α-hydroxy-11α,15α-bis-t-butyldimethylsilyloxy-
16-m-fluorophenoxy-17,18,19,20-tetranorprosta-
4,513-trans-treinoic acid,
(dl)-9α-hydroxy-11α,15α-bis-t-butyldimethylsilyloxy-
16-p-fluorophenoxy-17,18,19,20-tetranorprosta-
4,5,13-trans-trienoic acid,
(dl)-9α-hydroxy-11α,15α-bis-t-butyldimethylsilyloxy-
16-o-chlorophenoxy-17,18,19,20-tetranorprosta-
4,5,13-trans-trienoic acid,
(dl)-9α-hydroxy-11α,15α-bis-t-butyldimethylsilyloxy-
16-m-chlorophenoxy-17,18,19,20-tetranorprosta-
4,5,13-trans-trienoic acid,
(dl)-9α-hydroxy-11α,15α-bis-t-butyldimethylsilyloxy-
16-p-chlorophenoxy-17,18,19,20-tetranorprosta-
4,5,13-trans-trienoic acid,
(dl)-9α-hydroxy-11α,15α-bis-t-butyldimethylsilyloxy-
16-o-bromophenoxy-17,18,19,20-tetranorprosta-
4,5,13-trans-trienoic acid, (dl)-9α-hydroxy-11α,15α-bis-t-butyldimethylsilyloxy-16-m-bromophenoxy-17,18,19,20-tetranorprosta-4,5,13-trans-trienoic acid, (dl)-9α-hydroxy-11α,15α-bis-t-butyldimethylsilyloxy-16-p-bromophenoxy-17,18,19,20-tetranorprosta-4,5,13-trans-trienoic acid, (dl)-9α-hydroxy-11α,15α-bis-t-butyldimethylsilyloxy-16-o-methylphenoxy-17,18,19,20-tetranorprosta-4,5,13-trans-trienoic acid, (dl)-9α-hydroxy-11α,15α-bis-t-butyldimethylsilyloxy-16-m-methylphenoxy-17,18,19,20-tetranorprosta-4,5,13-trans-trienoic acid, (dl) -9α-hydroxy-11α,15α-bis-t-butyldimethylsilyloxy-16-p-methylphenoxy-17,18,19,20-tetranorprosta-4,5,13-trans-trienoic acid, (dl)-9α-hydroxy-11α,15α-bis-t-butyldimethylsilyloxy-16-o-methylphenoxy-17,18,19,20-tetranorprosta-4,5,13-trans-trienoic acid, (dl)-9α-hydroxy-11α,15α-bis-t-butyldimethylsilyloxy-16-m-methoxyphenoxy-17,18,19,20-tetranorprosta-4,5,13-trans-trienoic acid, (dl)-9α-hydroxy-11α,15α-bis-t-butyldimethylsilyloxy-16-p-methoxyphenoxy-17,18,19,20-tetranorprosta-4,5,13-trans-trienoic acid, for the methyl ester of (dl)-9α-hydroxy-11α,15α-bis-t-butyldimethylsilyloxy-16-phenoxy-17,18,19,20-tetranorprosta-4,5,13-trans-trienoic acid, there are obtained the methyl esters of (dl)-9-keto-11α,15α-bis-t-butyldimethylsilyloxy-16-o-fluorophenoxy-17,18,19,20-tetranorprosta-4,5,13-trans-trienoic acid, (dl)-9-keto-11α,15α-bis-t-butyldimethylsilyloxy-16-m-fluorophenoxy-17,18,19,20-tetranorprosta-4,5,13-trans-trienoic acid, (dl)-9-keto-11α,15α-bis-t-butyldimethylsilyloxy-16-p-fluorphenoxy-17,18,19,20-tetranorprosta-4,5,13-trans-trienoic acid, (dl)-9-keto-11α,15α-bis-t-butyldimethylsilyloxy-16-o-chlorophenoxy-17,18,19,20-tetranorprosta-4,5,13-trans-trienoic acid, (dl)-9-keto-11α,15α-bis-t-butyldimethylsilyloxy-16-m-chlorophenoxy-17,18,19,20-tetranorprosta-4,5,13-trans-trienoic acid, (dl)-9-keto-11α,15α-bis-t-butyldimethylsilyloxy-16-p-chlorophenoxy-17,18,19,20-tetranorprosta-4,5,13-trans-trienoic acid, (dl)-9-keto-11α,15α-bis-t-butyldimethylsilyloxy-16-o-bromophenoxy-17,18,19,20-tetranorprosta-4,5,13-trans-trienoic acid, (dl)-9-keto-11α,15α-bis-t-butyldimethylsilyloxy-16-m-bromophenoxy-17,18,19,20-tetranorprosta-4,5,13-trans-trienoic acid, (dl)-9-keto-11α,15α-bis-t-butyldimethylsilyloxy-16-p-bromophenoxy-17,18,19,20-tetranorprosta-4,5,13-trans-trienoic acid, (dl)-9-keto-11α,15α-bis-t-butyldimethylsilyloxy-16-o-methylphenoxy-17,18,19,20-tetranorprosta-4,5,13-trans-trienoic acid, (dl)-9-keto-11α,15α-bis-t-butyldimethylsilyloxy-16-m-methylphenoxy-17,18,19,20-tetranorprosta-4,5,13-trans-trienoic acid, (dl)-9-keto-11α,15α-bis-t-butyldimethylsilyloxy-16-p-methylphenoxy-17,18,19,20-tetranorprosta-4,5,13-trans-trienoic acid, (dl)-9-keto-11α,15α-bis-t-butyldimethylsilyloxy-16-o-methylphenoxy-17,18,19,20-tetranorprosta-4,5,13-trans-trienoic acid, (dl)-9-keto-11α,15α-bis-t-butyldimethylsilyloxy-16-m-methylphenoxy-17,18,19,20-tetranorprosta-4,5,13-trans-trienoic acid, and (dl)-9-keto-11α,15α-bis-t-butyldimethylsilyloxy-16-p-methylphenoxy-17,18,19,20-tetranorprosta-4,5,13-trans-trienoic acid, respectively.

In like manner other esters otherwise corresponding to the above-identified starting compounds can be converted to the corresponding ester 9-keto-11α,15α-bis-t-butyldimethylsilyloxy compounds.

EXAMPLE 3

A solution of 230 mg. of (dl)-9-keto-11α,15α-bis-t-butyldimethylsilyloxy-16-phenoxy-17,18,19,20-tetranorprosta-4,5,13-trans-trienoic acid methyl esters (3) in 260 ml. of acetic acid containing 140 ml. of water is stirred at 20°–25° C. for 15–20 hours.

The acetic acid-water is removed under reduced pressure followed by reduced pressure azeotropic distillation using 100 ml of toluene. The oily residue is chromatographed on a silica gel column and eluted with ethyl acetate-hexane (25/75:100/0) to yield (dl)-9-keto-11α,15α-dihydroxy-16-phenoxy-17,18,19,20-tetranorprosta-4,5,13-trans-trienoic acid methyl ester (4) having the following physical constants:

U.V. $\lambda_{max}^{MeOH}$ 220, 265, 271, 277 nm (log ε 4.01, 3.14, 3.24 3.16) (ε 10,218, 1388, 1732, 1440);

N.M.R. $\delta_{TMS}^{CDCl_3}$ 3.63 (s, 3H, OCH$_3$) 3.85–4.2 (m, 3H, H-11, 16) 4.55 (m, 1H, H-15) 5.07 (m, 2H, H-13,14) 6.8–7.05 (m, 3H, aromatic-H) 7.15–7.38 (m, 3H, aromatic - H); and M.S. m/e 400 (M+).

In like manner, substituting a stoichiometric equivalent amount of the methyl esters of (dl)-9-keto-11α,15α-bis-t-butyldimethylsilyloxy-16-o-fluorophenoxy-17,18,19,20-tetranorprosta-4,5,13-trans-trienoic acid, (dl)-9-keto-11α,15α-bis-t-butyldimethylsilyloxy-16-m-fluorophenoxy-17,18,19,20-tetranorprosta-4,5,13-trans-trienoic acid, (dl)-9-keto-11α,15α-bis-t-butyldimethylsilyloxy-16-p-fluorophenoxy-17,18,19,20-tetranorprosta-4,5,13-trans-trienoic acid, (dl)-9-keto-11α,15α-bis-t-butyldimethylsilyloxy-16-o-chlorophenoxy-17,18,19,20-tetranorprosta-4,5,13-trans-trienoic acid, (dl)-9-keto-11α,15α-bis-t-butyldimethylsilyloxy-16-m-chlorophenoxy-17,18,19,20-tetranorprosta-4,5,13-trans-trienoic acid, (dl)-9-keto-11α,15α-bis-t-butyldimethylsilyloxy-16-p-chlorophenoxy-17,18,19,20-tetranorprosta-4,5,13-trans-trienoic acid, (dl)-9-keto-11α,15α-bis-t-butyldimethylsilyloxy-16-o-bromophenoxy-17,18,19,20-tetranorprosta-4,5,13-trans-trienoic acid, (dl)-9-keto-11α,15α-bis-t-butyldimethylsilyloxy-16-m-bromophenoxy-17,18,19,20-tetranorprosta-4,5,13-trans-trienoic acid, (dl)-9-keto-11α,15α-bis-t-butyldimethylsilyloxy-16-p-bromophenoxy-17,18,19,20-tetranorprosta-4,5,13-trans-trienoic acid, (dl)-9-keto-11α,15α-bis-t-butyldimethylsilyloxy-16-o-methylphenoxy-17,18,19,20-tetranorprosta-4,5,13-trans-trienoic acid, (dl)-9-keto-11α,15α-bis-t-butyldimethylsilyloxy-16-m-methylphenoxy-17,18,19,20-tetranorprosta-4,5,13-trans-trienoic acid, (dl)-9-keto-11α,15α-bis-t-butyldimethylsilyloxy-16-p-methylphenoxy-17,18,19,20-tetranorprosta-4,5,13-trans-trienoic acid, (dl)-9-keto-11α,15α-bis-t-butyldimethylsilyloxy-16-o-methoxyphenoxy-17,18,19,20-tetranorprosta-4,5,13-trans-trienoic acid, (dl)-9-keto-11α,15α-bis-t-butyldimethylsilyloxy-16-m-methoxyphenoxy-17,18,19,20-tetranorprosta-4,5,13-trans-trienoic acid, and (dl)-9-keto-11α,15α-bis-t-butyldimethylsilyloxy-16-p-methoxyphenoxy-17,18,19,20-tetranorprosta-4,5,13-trans-trienoic acid, for the methyl ester of 9-keto-11α,15α-bis-t-butyldimethylsilyloxy-16-phenoxy-17,18,19,20-tetranorprosta-4,5,13-trans-trienoic acid, there are obtained the methyl esters of (dl)-9-keto-11α,15α-dihydroxy-16-o-fluorophenoxy-17,18,19,20-tetranorprosta-4,5,13-trans-trienoic acid, (dl)-9-keto-11α,15α-dihydroxy-16-m-fluorophenoxy-17,18,19,20-tetranorprosta-4,5,13-trans-trienoic acid, (dl)-9-keto-11α,15α-dihydroxy-16-p-fluorophenoxy-17,18,19,20-tetranorprosta-4,5,13-trans-trienoic acid, (dl)-9-keto-11α,15α-dihydroxy-16-o-chlorophenoxy-17,18,19,20-tetranorprosta-4,5,13-trans-trienoic acid, (dl)-9-keto-11α,15α-dihydroxy-16-m-chlorophenoxy-17,18,19,20-tetranorprosta-4,5,13-trans-trienoic acid, (dl)-9-keto-11α,15α-dihydroxy-16-p-chlorophenoxy-17,18,19,20-tetranorprosta-4,5,13-trans-trienoic acid, (dl)-9-keto-11α,15α-dihydroxy-16-o-bromophenoxy-17,18,19,20-tetranorprosta-4,5,13-trans-trienoic acid, (dl)-9-keto-11α,15α-dihydroxy-16-m-bromophenoxy-17,18,19,20-tetranorprosta-4,5,13-trans-trienoic acid, (dl)-9-keto-11α,15α-dihydroxy-16-p-bromophenoxy-17,18,19,20-tetranorprosta-4,5,13-trans-trienoic acid, (dl)-9-keto-11α,15α-dihydroxy-16-o-methylphenoxy-17,18,19,20-tetranorprosta-4,5,13-trans-trienoic acid, (dl)-9-keto-11α,15α-dihydroxy-16-m-methylphenoxy-17,18,19,20-tetranorprosta-4,5,13-trans-trienoic acid, (dl)-9-keto-11α,15α-dihydroxy-16-p-methylphenoxy-17,18,19,20-tetranorprosta-4,5,13-trans-trienoic acid, (dl)-9-keto-11α,15α-dihydroxy-16-o-methoxyphenoxy-17,18,19,20-tetranorprosta-4,5,13-trans-trienoic acid, (dl)-9-keto-11α,15α-dihydroxy-16-m-methoxyphenoxy-17,18,19,20-tetranorprosta-4,5,13-trans-trienoic acid, and (dl)-9-keto-11α,15α-dihydroxy-16-p-methoxyphenoxy-17,18,19,20-tetranorprosta-4,5,13-trans-trienoic acid, respectively.

In like manner other esters otherwise corresponding to the above-identified starting compounds can be converted to the corresponding ester 9-keto-11α,15α-hydroxy compounds.

EXAMPLE 4

50 Mg. of (dl)-9-keto-11α,15α-dihydroxy-16-phenoxy-17,18,19,20-tetranorprosta-4,5,13-trans-trienoic acid methyl ester (4) is mixed with 20 ml. of a pancreatic lipase preparation, prepared according to Preparation 1, at room temperature. The mixture is emulsified by sonication for five minutes and then stirred at room temperature for thirty minutes. The mixture is poured into 125 ml. of acetone, filtered and evaporated, under vacuum, and the resulting residue is extracted with four 25 ml. portions of ethyl acetate. The extracts are combined and concentrated by vacuum evaporation. The concentrate is chromatographed on silica gel thin-layer plates using a 1:1 (volume proportion) of chloroform:methanol. The product is removed from the silica gel with a 3:1 (volume proportion) of ethyl acetate:methanol. Following filtration and vacuum evaporation of the solvent there is obtained (dl)-9-keto-11α,15α-dihydroxy-16-phenoxy-17,18,19,20-tetranorprosta-4,5,13-trans-trienoic acid (5).

Similarly, substituting a stoichiometric equivalent amount of the methyl esters of (dl)-9-keto-11α,15α-dihydroxy-16-o-fluorophenoxy-17,18,19,20-tetranorprosta-4,5,13-trans-trienoic acid, (dl)-9-keto-11α,15α-dihydroxy-16-m-fluorophenoxy-17,18,19,20-tetranorprosta-4,5,13-trans-trienoic acid, (dl)-9-keto-11α,15α-dihydroxy-16-p-fluorophenoxy-17,18,19,20-tetranorprosta-4,5,13-trans-trienoic acid, (dl)-9-keto-11α,15α-dihydroxy-16-o-chlorophenoxy-17,18,19,20-tetranorprosta-4,5,13-trans-trienoic acid, (dl)-9-keto-11α,15α-dihydroxy-16-m-chlorophenoxy-17,18,19,20-tetranorprosta-4,5,13-trans-trienoic acid, (dl)-9-keto-11α,15α-dihydroxy-16-p-chlorophenoxy-17,18,19,20-tetranorprosta-4,5,13-trans-trienoic acid, (dl)-9-keto-11α,15α-dihydroxy-16-o-bromophenoxy-17,18,19,20-tetranorprosta-4,5,13-trans-trienoic acid, (dl)-9-keto-11α,15α-dihydroxy-16-m-bromophenoxy-17,18,19,20-tetranorprosta-4,5,13-trans-trienoic acid, (dl)-9-keto-11α,15α-dihydroxy-16-p-bromophenoxy-17,18,19,20-tetranorprosta-4,5,13-trans-trienoic acid, (dl)-9-keto-11α,15α-dihydroxy-16-o-methylphenoxy-17,18,19,20-tetranorprosta-4,5,13-trans-trienoic acid, (dl)-9-keto-11α,15α-dihydroxy-16-m-methylphenoxy-17,18,19,20-tetranorprosta-4,5,13-trans-trienoic acid, (dl)-9-keto-11α,15α-dihydroxy-16-p-methylphenoxy-17,18,19,20-tetranorprosta-4,5,13-trans-trienoic acid, (dl)-9-keto-11α,15α-dihydroxy-16-o-methoxyphenoxy-17,18,19,20-tetranorprosta-4,5,13-trans-trienoic acid, (dl)-9-keto-11α,15α-dihydroxy-16-m-methoxyphenoxy-17,18,19,20-tetranorprosta-4,5,13-trans-trienoic acid, and (dl)-9-keto-11α,15α-dihydroxy-16-p-methoxyphenoxy-17,18,19,20-tetranorprosta-4,5,13-trans-trienoic acid, for the methyl ester of (dl)-9-keto-11α,15α-dihydroxy-16-o-phenoxy-17,18,19,20-tetranorprosta-4,5,13-trans-trienoic acid, there are obtained (dl)-9-keto-11α,15α-dihydroxy-16-o-fluorophenoxy-17,18,19,20-tetranorprosta-4,5,13-trans-trienoic acid, (dl)-9-keto-11α,15α-dihydroxy-16-m-fluorophenoxy-17,18,19,20-tetranorprosta-4,5,13-trans-trienoic acid, (dl)-9-keto-11α,15α-dihydroxy-16-p-fluorophenoxy-17,18,19,20-tetranorprosta-4,5,13-trans-trienoic acid, (dl)-9-keto-11α,15α-dihydroxy-16-o-chlorophenoxy-17,18,19,20-tetranorprosta-4,5,13-trans-trienoic acid, (dl)-9-keto-11α,15α-dihydroxy-16-m-chlorophenoxy-17,18,19,20-tetranorprosta-4,5,13-trans-trienoic acid, (dl)-9-keto-11α,15α-dihydroxy-16-p-chlorophenoxy-17,18,19,20-tetranorprosta-4,5,13-trans-trienoic acid, (dl)-9-keto-11α,15α-dihydroxy-16-o-bromophenoxy-17,18,19,20-tetranorprosta-4,5,13-trans-trienoic acid, (dl)-9-keto-11α,15α-dihydroxy-16-m-bromophenoxy-17,18,19,20-tetranorprosta-4,5,13-trans-trienoic acid, (dl)-9-keto-11α,15α-dihydroxy-16-p-bromophenoxy-17,18,19,20-tetranorprosta-4,5,13-trans-trienoic acid, (dl)-9-keto-11α,15α-dihydroxy-16-o-methylphenoxy-17,18,19,20-tetranorprosta-4,5,13-trans-trienoic acid, (dl)-9-keto-11α,15α-dihydroxy-16-m-methylphenoxy-17,18,19,20-tetranorprosta-4,5,13-trans-trienoic acid, (dl)-9-keto-11α,15α-dihydroxy-16-p-methylphenoxy-17,18,19,20-tetranorprosta-4,5,13-trans-trienoic acid, (dl)-9-keto-11α,15α-dihydroxy-16-o-methoxyphenoxy-17,18,19,20-tetranorprosta-4,5,13-trans-trienoic acid, (dl)-9-keto-11α,15α-dihydroxy-16-m-methoxyphenoxy-17,18,19,20-tetranorprosta-4,5,13-trans-trienoic acid, and (dl)-9-keto-11α,15α-dihydroxy-16-p-methoxyphenoxy-17,18,19,20-tetranorprosta-4,5,13-trans-trienoic acid, respectively.

In like manner other esters otherwise corresponding to the above-identified starting compounds can be converted to the corresponding free acid 9-keto-11α,15α-dihydroxy compounds.

EXAMPLE 5

To a solution of 92 mg. of (dl)-9-keto-11α,15α-dihydroxy-16-phenoxy-17,18,19,20-tetranorprosta-4,5,13-trans-trienoic acid in 10 ml. of methanol is added 1.0 molar equivalents of a 0.1 N solution of sodium bicarbonate and the mixture is stirred at room temperature for 1 hour. The reaction mixture is then evaporated to dryness under reduced pressure, to give the sodium salt of (dl)-9-keto-11α,15α-dihydroxy-16-phenoxy-17,18,19,20-tetranorprosta-4,5,13-trans-trienoic acid.

By employing 1.0 molar equivalents of potassium bicarbonate (in the form of a 0.1 N solution) in place of sodium bicarbonate in the above procedure, the potassium salt of (dl)-9-keto-11α,15α-dihydroxy-16-phenoxy-17,18,19,20-tetranorprosta-4,5,13-trans-trienoic acid is obtained.

Similarly, the sodium and potassium salts of the other 9-keto-prostatrienoic acid compounds obtained in Example 4, i.e., (dl)-9-keto-11α,15α-dihydroxy-16-o-fluorophenoxy-17,18,19,20-tetranorprosta-4,5,13-trans-trienoic acid,
(dl)-9-keto-11α,15α-dihydroxy-16-m-fluorophenoxy-17,18,19,20-tetranorprosta-4,5,13-trans-trienoic acid,
(dl)-9-keto-11α,15α-dihydroxy-16-p-fluorophenoxy-17,18,19,20-tetranorprosta-4,5,13-trans-trienoic acid,
(dl)-9-keto-11α,15α-dihydroxy-16-o-chlorophenoxy-17,18,19,20-tetranorprosta-4,5,13-trans-trienoic acid,
(dl)-9-keto-11α,15α-dihydroxy-16-m-chlorophenoxy-17,18,19,20-tetranorprosta-4,5,13-trans-trienoic acid,
(dl)-9-keto-11α,15α-dihydroxy-16-p-chlorophenoxy-17,18,19,20-tetranorprosta-4,5,13-trans-trienoic acid,
(dl)-9-keto-11α,15α-dihydroxy-16-o-bromophenoxy-17,18,19,20-tetranorprosta-4,5,13-trans-trienoic acid,
(dl)-9-keto-11α,15α-dihydroxy-16-m-bromophenoxy-17,18,19,20-tetranorprosta-4,5,13-trans-trienoic acid,
(dl)-9-keto-11α,15α-dihydroxy-16-p-bromophenoxy-17,18,19,20-tetranorprosta-4,5,13-trans-trienoic acid,
(dl)-9-keto-11α,15α-dihydroxy-16-o-methylphenoxy-17,18,19,20-tetranorprosta-4,5,13-trans-trienoic acid,
(dl)-9-keto-11α,15α-dihydroxy-16-m-methylphenoxy-17,18,19,20-tetranorprosta-4,5,13-trans-trienoic acid,
(dl)-9-keto-11α,15α-dihydroxy-16-p-methylphenoxy-17,18,19,20-tetranorprosta-4,5,13-trans-trienoic acid,
(dl)-9-keto-11α,15α-dihydroxy-16-o-methoxyphenoxy-17,18,19,20-tetranorprosta-4,5,13-trans-trienoic acid,
(dl)-9-keto-11α,15α-dihydroxy-16-m-methoxyphenoxy-17,18,19,20-tetranorprosta-4,5,13-trans-trienoic acid, and
(dl)-9-keto-11α,15α-dihydroxy-16-p-methoxyphenoxy-17,18,19,20-tetranorprosta-4,5,13-trans-trienoic acid, are obtained.

EXAMPLE 6

To a solution of 20 mg. of (dl)-9-keto-11α,15α-dihydroxy-16-phenoxy-17,18,19,20-tetranorprosta-4,5,13-trans-trienoic acid in 5 ml. of methanol is added a mixture of 1 ml. of concentrated ammonium hydroxide solution and 2 ml. of methanol. The resulting mixture is stirred for two hours at room temperature and then evaporated to dryness, to yield the ammonium salt of (dl)-9-keto-11α,15α-dihydroxy-16-phenoxy-17,18,19,20-tetranorprosta-4,5,13-trans-trienoic acid.

By employing dimethylamine, diethylamine or dipropylamine in place of ammonium hydroxide in the above procedure, the corresponding salts of (dl)-9-keto-11α,15α-dihydroxy-16-phenoxy-17,18,19,20-tetranorprosta-4,5,13-trans-trienoic acid are obtained.

In a similar manner, the ammonium, dimethylamine, diethylamine and dipropylamine salts of the other 9-keto-prostatrienoic acid compounds of Example 4 can be prepared.

EXAMPLE 7

To a mixture of 30.6 mg. of procaine (1.0 molar equivalent) and 1.5 ml. of aqueous methanol is added 50 mg. of (dl)-9-keto-11α,15α-dihydroxy-16-phenoxy-17,18,19,20-tetranorprosta-4,5,13-trans-trienoic acid in 10 ml. of methanol and the resultant reaction mixture is stirred at room temperature for 16 hours. It is then evaporated to dryness under reduced pressure to give the procaine salt of (dl)-9-keto-11α,15α-dihydroxy-16-phenoxy-17,18,19,20-tetranorprosta-4,5,13-trans-trienoic acid.

Similarly, the lysine, caffeine, tromethamine, and arginine salts thereof are obtained.

In like manner, the procaine, lysine, caffeine, tromethamine, and arginine salts of other 9-keto-prostatrienoic acid compounds obtained in Example 4 can be prepared.

What is claimed is:

1. A compound selected from the group of those represented by the following formula:

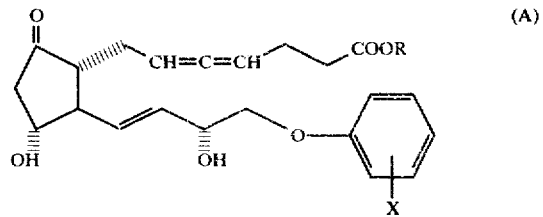

wherein
R is hydrogen, a lower alkyl group of 1 to 4 carbon atoms, or the pharmaceutically acceptable, nontoxic salts of compounds in which R is hydrogen; and
X is hydrogen, o-, m-, or p-halo (fluoro, chloro or bromo), o-, m- or p-methyl or o-, m- or p-methoxy.

2. A compound according to claim 1 wherein R is hydrogen and X is hydrogen, (dl)-9-keto-11α,15α-dihydroxy-16-phenoxy-17,18,19,20-tetranorprosta-4,5,13-trans-trienoic acid.

3. A compound according to claim 1 wherein R is methyl and X is hydrogen, (dl)-9-keto-11α,15α -dihydroxy-16-phenoxy-17,18,19,20-tetranorprosta-4,5,13-trans-trienoic acid methyl ester.

4. A sodium salt compound according to claim 1 where X is hydrogen, (dl)-9-keto-11α,15α-dihydroxy-16-phenoxy-17,18,19,20-tetranorprosta-4,5,13-trans-trienoic acid sodium salt.

5. A compound according to claim 1 wherein R is hydrogen and X is o-fluoro, (dl)-9-keto-11α,15α-dihydroxy-16-o-fluorophenoxy-17,18,19,20-tetranorprosta-4,5,13-trans-trienoic acid.

6. A compound according to claim 1 where R is hydrogen and X is m-chloro, (dl)-9-keto-11α,15α-dihydroxy-16-m-chlorophenoxy-17,18,19,20-tetranorprosta-4,5,13-trans-trienoic acid.

7. A compound according to claim 1 wherein R is hydrogen and X is p-methyl, (dl)-9-keto-11α,15α-dihydroxy-16-p-methylphenoxy-17,18,19,20-tetranorprosta-4,5,13-trans-trienoic acid.

8. A compound according to claim 1 wherein R is hydrogen and X is m-methoxy, (dl)-9-keto-11α,15α-dihydroxy-16-m-methoxyphenoxy-17,18,19,20-tetranorprosta-4,5,13-trans-trienoic acid.

9. A compound according to claim 1 wherein R is hydrogen and $R^2$ is p-fluoro, (dl)-9-keto-11α,15α-dihydroxy-16-p-fluorophenoxy-17,18,19,20-tetranorprosta-4,5,13-trans-trienoic acid.

10. A compound according to claim 1 wherein R is hydrogen and X is o-chloro, (dl)-9-keto-11α,15α-dihydroxy-16-o-chlorophenoxy-17,18,19,20-tetranorprosta-4,5,13-transtrienoic acid.

* * * * *